United States Patent [19]

Faisandier

[11] 4,137,940
[45] Feb. 6, 1979

[54] LIQUID FLOW CONTROL APPARATUS

[75] Inventor: Yves Faisandier, Montrouge, France

[73] Assignee: Societe CM Industries, Paris, France

[21] Appl. No.: 734,769

[22] Filed: Oct. 22, 1976

[30] Foreign Application Priority Data

Nov. 5, 1975 [FR] France .................................. 75 33850

[51] Int. Cl.² .............................................. G05D 7/06
[52] U.S. Cl. ................................. 137/486; 137/487.5;
137/551
[58] Field of Search .................. 137/487.5, 486, 551

[56] References Cited

U.S. PATENT DOCUMENTS

| 3,163,176 | 12/1964 | Darling | 137/487.5 |
| 3,450,153 | 6/1969 | Hildebrandt | 137/487.5 X |
| 3,601,124 | 8/1971 | Petree | 137/487.5 X |
| 3,990,443 | 11/1976 | Fletcher | 137/487.5 X |

*Primary Examiner*—Alan Cohan
*Attorney, Agent, or Firm*—Bucknam and Archer

[57] ABSTRACT

There is disclosed liquid flow control apparatus (particularly for use where the flow takes place in the form of drops over at least part of the flow path). A valve in the flow path is controlled by a servo system in dependence on the difference between desired and actual rate of flow signals. A linear to exponential signal converter sets the desired rate of flow signal which is displayed by means of two relatively movable display members one of which is movable to a position dependent on the desired rate of flow and carries a logarithmic scale which is juxtaposed with a logarithmic scale on the other member. For example, the other member may be movable to a position dependent on the size of the drops, and the volume rate of liquid flow for any given time can be read off from the juxtaposed scale. The apparatus also includes a throttle valve comprising two relatively movable throttling members positioned on opposite sides of a flexible tube. One member is pivotable about an axis parallel with the flexible tube and the other is slidably urged towards the tube.

6 Claims, 7 Drawing Figures

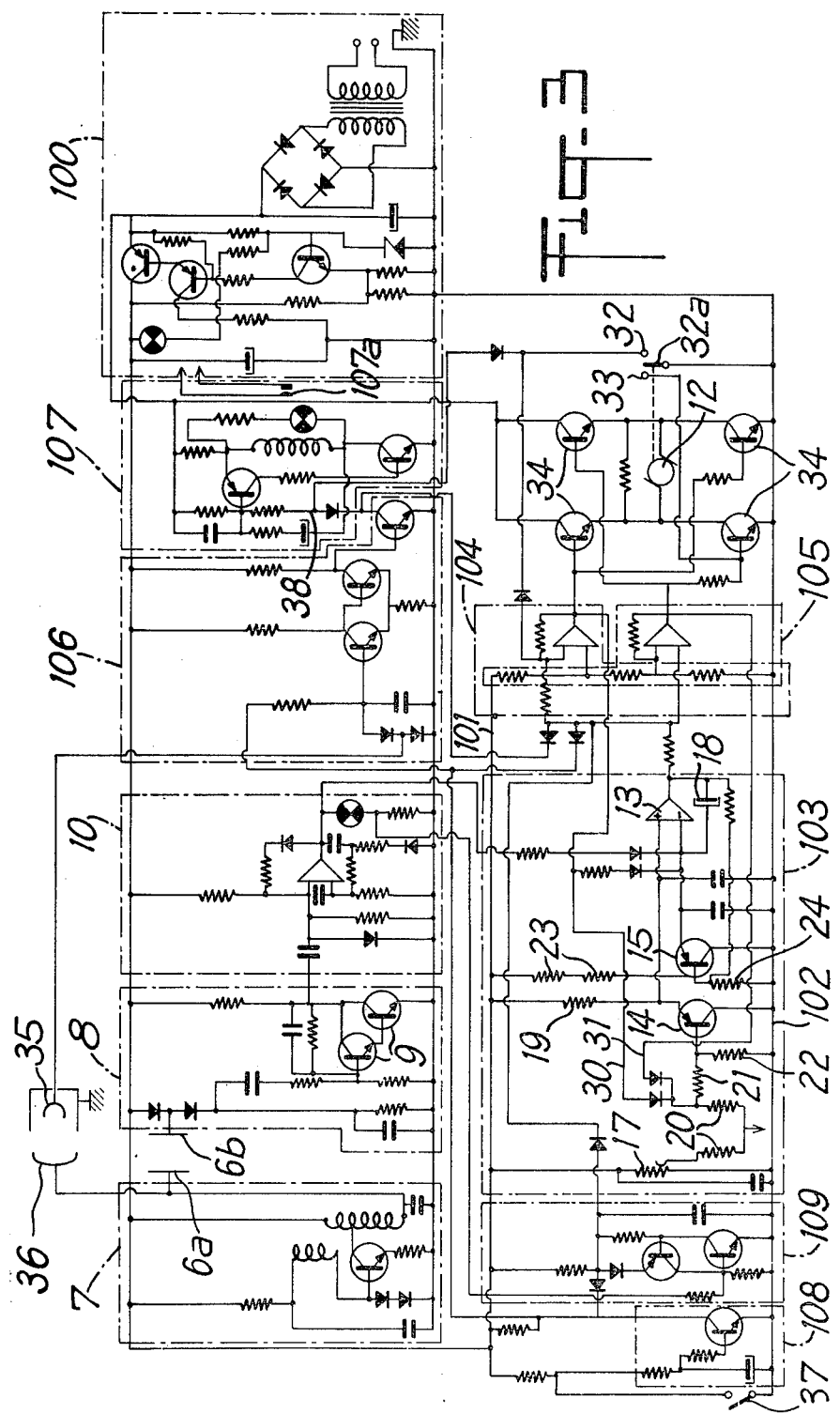

LIQUID FLOW CONTROL APPARATUS

BACKGROUND OF THE INVENTION

The invention relates to liquid flow control apparatus such as, for example, for use in perfusion or transfusion applications.

More particularly, it relates to such apparatus in which there is provided a liquid flow path incorporating an adjustable flow control valve, the valve being controlled by servo means.

It is an object of the invention to provide improved liquid flow control apparatus.

SUMMARY OF THE INVENTION

According to the invention, there is provided liquid flow control apparatus, comprising means defining a liquid flow path, flow control valve means in the said path for varying the rate of liquid flow therein, a rate of flow detector arranged to produce an actual rate of flow signal dependent on the actual rate of the said liquid flow in the flow path, setting means for producing a desired rate of flow signal, and servo control means for comparing the two said signals to produce an error signal and including means responsive to the error signal for adjusting the valve means in such a sense such as to tend to control the rate of liquid flow at the desired rate, the said setting means including linear to exponential signal converting means and two relatively movable display members one of which is movable to a position dependent on the desired rate of flow and carries a logarithmic scale which is juxtaposed with a logarithmic scale on the other member to enable a parameter related to the desired rate of flow to be determined by the relative positions of the two logarithmic scales.

According to the invention, there is also provided liquid flow control apparatus, comprising means defining a liquid flow path, flow control valve means in the said path for varying the rate of liquid flow along the flow path, a rate of flow detector in the said path and upstream of the valve means and arranged to produce an actual rate of flow signal in terms of the rate of flow of liquid drops along the said path, setting means for producing a desired rate of flow signal in terms of a desired rate of flow of drops, and servo-control means for comparing the two said signals to produce an error signal and including means responsive to the error signal for controlling the valve means in a sense such as to tend to control the rate of liquid flow at the said desired rate, the said setting means comprising two relatively movable display members one of which is movable, independently of the other, to a position dependent on the said desired rate of flow and carries a logarithmic scale, the other of which carries a logarithmic scale and is movable, independently of the said one member, to a position determined in accordance with the size of the said drops, the two logarithmic scales being juxtaposed with each other and arranged so as to enable the rate of liquid flow in terms of volume per unit time to be read off from the two juxtaposed logarithmic scales.

According to the invention, there is further provided liquid flow control apparatus, comprising a flexible tube for carrying the liquid, and a throttle valve for variably throttling the tube, the throttle valve comprising two throttling elements mounted in contact with opposite sides of the flexible tube and movable towards and away from each other so as variably to throttle the said tube, one said element being pivotable about an axis which is not at right angles to the plane of contact of this element with the flexible tube, and the other said element being slidable along an axis which is not parallel to its plane of contact with the flexible tube and being resiliently biased towards the tube, and means for pivoting the first element around its said axis so as to vary the throttling effect on the said tube.

BRIEF DESCRIPTION OF THE DRAWINGS

A flow control device embodying the invention will now be described by way of example only and with reference to the accompanying drawings, in which:

FIG. 3 is a complete diagram of the circuits of the device;

DESCRIPTION OF PREFERRED EMBODIMENTS

Figure 1:
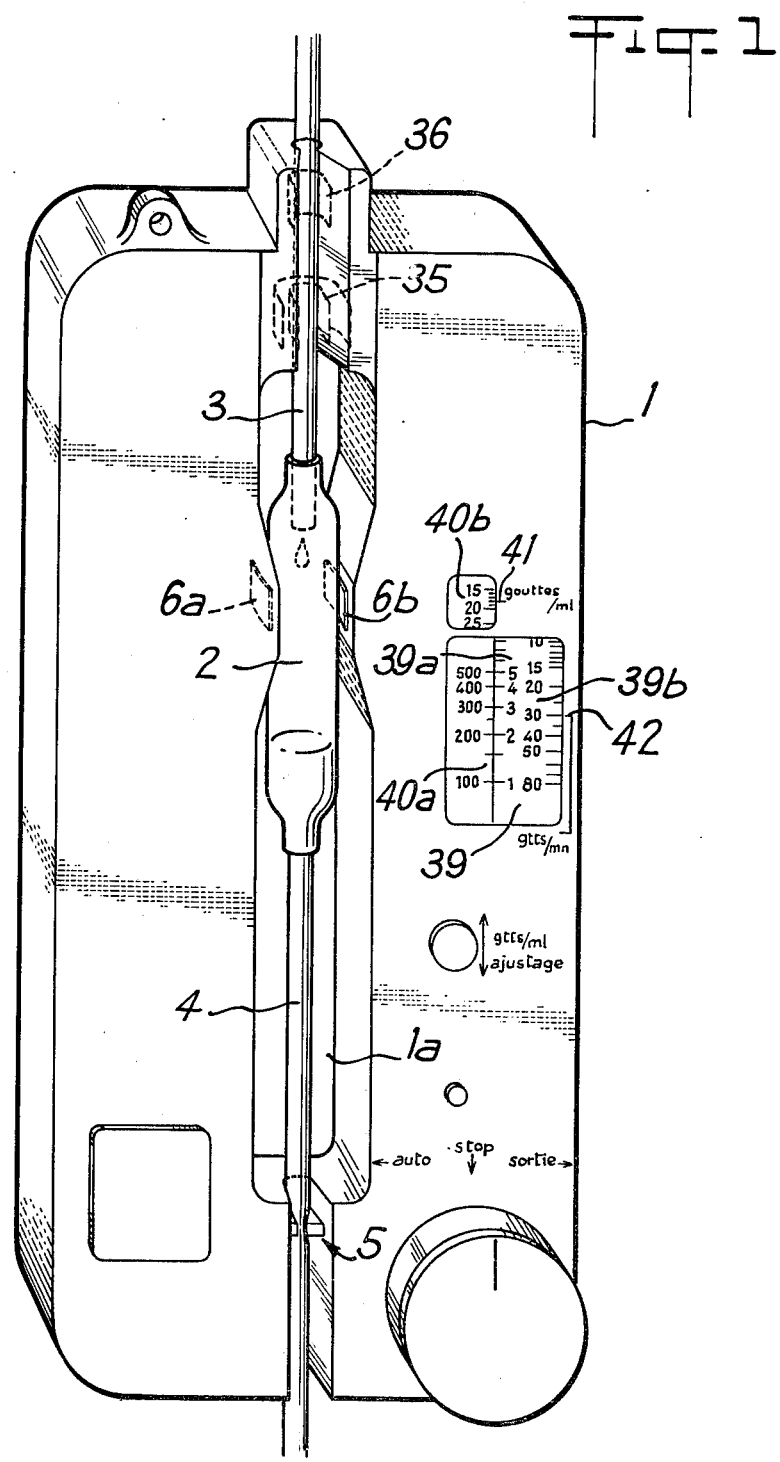
FIG. 1 is a front view of the case of the flow control device.
Figure 2:
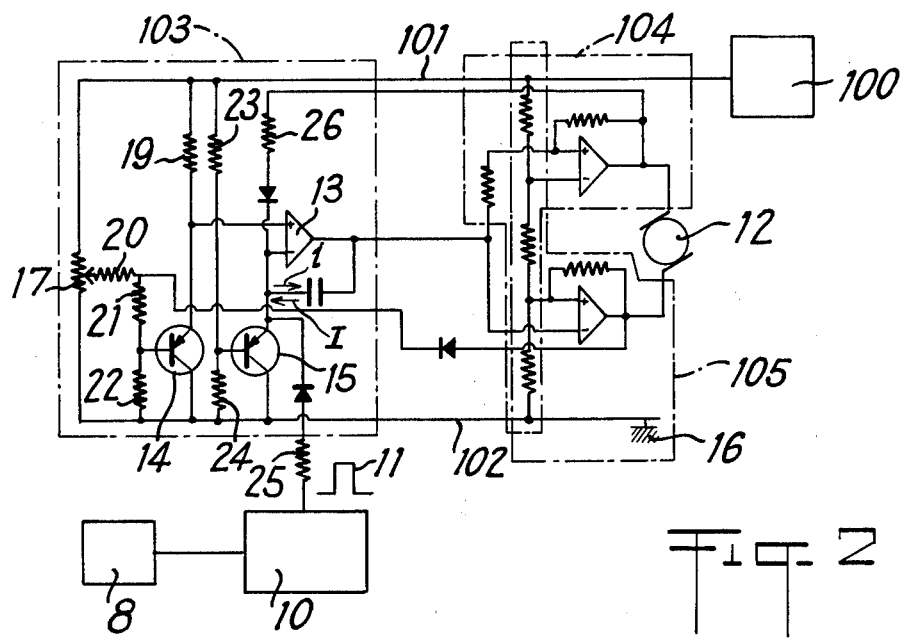
FIG. 2 is a simplified diagram of the electronic circuits of the device.

FIGS. 1 to 6 illustrate a device for controlling the rate of flow of liquid in a pipe such as a transfusion or perfusion pipe. The device forms a sufficiently light assembly to be hung from a standard perfusion or transfusion tube, and comprises:

(1) a drop detector;
(2) an electronic servo-control unit which receives the data from the detector and which produces an error signal representing the difference between the rate of flow measured and the rate of flow required;
(3) a system for throttling the delivery tube of the transfusion tube, this system forming a throttle valve controlled by the error signal;
(4) warning means operating when the true rate of flow of liquid does not reach the rate of flow required; and
(5) warning means operating in the case of presence of air in the inflow tube of the perfusion piping.

The assembly has a case 1 of plastics material having a frame centrally cut away at 1a to receive the chamber 2 of a transfusion system comprising, in known manner, a drop-by-drop flow chamber 2, a liquid infeed tube 3 and a flexible delivery tube 4. The case 1 is placed over the chamber 2 and secured on the liquid infeed tube 3, and clamps the delivery tube 4 (FIG. 1) by means of the throttling system 5. The device thus assembled is ready for use.

The drop detector indicates the fall of each drop in the chamber 2 and operates in accordance with the principle of a liquid displacement detector. The detector (FIGS. 2 and 3) comprises a direct-current stabilised supply 100, an electrostatic detector for detecting the presence of liquid comprising two plate-shaped electrodes 6a, 6b which are arranged at either side of the chamber 2 and whose signals are amplified, an oscillator 7 connected to the electrode 6a, a circuit 8 for detecting and amplifying a signal representing the current passing through the capacitor formed by the electrodes 6a, 6b, and a monostable flipflop 10 for shaping the signals emerging from the circuit 8.

An output signal of rectangular shape is thus supplied by the detector 100, 6a, 6b, 7 to 10, in response to each drop within the chamber 2.

A satisfactory signal/noise ratio for this detector is obtained by passing a relatively powerful current (1μA) through the detection capacitor formed by the two electrodes 6a, 6b. To this end, the oscillator 7 is of the type generating a peak to peak voltage of approximately 100 V, at a frequency of 1 MHz. The circuit 8 comprises a diode pump circuit and an amplifier with two transistors 9 connected in Darlington configuration.

The voltage signal produced in the circuit 8 and amplified by the transistors 9 is shaped in the monostable flipflop 10. The pulse signal emerging from the monostable flipflop 10 is fed to an electronic servo-control unit which is connected between a conductor 101 connected to the output terminal 100 of the supply and a conductor 102 earthed at 16 and comprises circuits which perform the following functions with relatively few components:-

(1) The function of a double-slope differential integrator for comparing a displayed desirable frequency and an actual frequency of drops, and producing an error signal.

(2) The linear to exponential conversion of a desirable frequency input signal allowing logarithmic display of the desirable frequency.

(3) The transmission of constant amplitude control pulses to a motor 12 controlling the throttle valve, every time the difference between the frequencies is not zero, the frequency and amplitude of these control pulses being a function of the magnitude of the difference.

The function of the double-slope differential integrator is performed by a circuit 103 comprising an operational amplifier 13, each input of this amplifier 13 being connected to the emitter of a corresponding transistor 14, 15 whose collector is earthed at 16 and whose base is energised at a particular potential which is constant in the case of the transistor 15 and which is adjustable by means of the potentiometer 17 in the case of the transistor 14, transistor 15 being associated with the inverting input of the operational amplifier 13. A capacitor 18 is feedback-connected between the output and the inverting input of the amplifier 13 which is arranged in such a manner that it always operates in unsaturated mode, that is to say that its two inputs are always practically at the same potential.

The operational amplifier 13 charges the capacitor 18 by means of the current I traversing the transistor 15. This current is determined by the relationship:

$$I = I_o \, e^{(U-\text{Ref.})(Q/KT)}$$

in which K is Boltzman's constant, T the temperature and Q the electron charge. Io is a constant value current supplied by a current generator 19 which is connected to the non-inverting input of the amplifier 13 and which may be formed by a simple resistor connected between that input and the supply conductor 101. The current I is thus an exponential function of the difference between U and Ref. U is the control voltage of the transistor 14, that is to say a fraction of the voltage at the top of the control potentiometer 17, obtained by means of the potential divider formed by the resistors 20, 21 on the one hand and the resistor 22 on the other hand. Ref. is the constant base voltage of the transistor 15 obtained by means of the potential divider provided by the resistors 23 and 24.

The discharge of the capacitor 18 is caused at each transmission through the resistor 25 by the monostable flipflop 10 of a "calibrated" pulse 11 having a period t.

The current pulse applied to the emitter of the transistor 15 is greater than the current I which may be set up in the emitter-collector circuit of the transistor 15 so that a discharge current $i$ is set up across the capacitor 18 and discharges the latter by a particular voltage. When the charge of the capacitor 18 balances its periodic discharge, the output level of the amplifier 13 oscillates in sawtooth form around a mean level.

Triggering into rotation, in an appropriate sense, of the motor 13 occurs when the discharge of the capacitor 18 becomes unequal to its charge. To this end, two bistable comparators 104 and 105 analyse the output voltage of the amplifier 13: the comparator 104 detects the case when the charging of the capacitor exceeds its discharging, and the comparator 105 detects the opposite condition.

The comparators 104 and 105 comprise an operational amplifier arranged as a Schmidt trigger.

When the comparator 104 comes into action, it directs a control pulse 27 to the motor 12, whose period is determined by the resistor 26 which discharges the capacitor 18 to a value such as to cause the comparator 104 to return to the "low" state. To ensure this operation, the output of the comparator 104 is connected via the resistor 26 to the inverting terminal of the amplifier 13.

Each control pulse 27 engenders such rotation of the motor 12 as to produce an opening of the clamping system forming the throttle valve 5.

Figure 4:
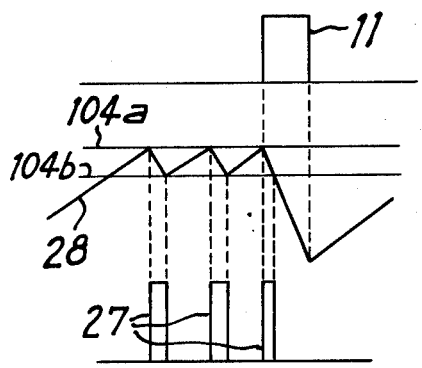
FIG. 4 is a graph showing error detection and device control signals in the case in which the true rate of flow is excessive.

As far as pulse 11 of the monostable flipflop is concerned, FIG. 4 shows the graph of the output level 28 of the amplifier 13 and of the control pulses 27 obtained in response to the effect of opening the throttle valve. It is observed that the frequency of the control pulses 27, when there is no fall of drops, that is to say in the absence of pulses 11 from the monostable flipflip, is a function of the charge gradient of the capacitor 18, consequently of the displayed desirable rate of flow; it is plain that the comparator 104 has an activation level 104a which exceeds its deactivation (or zero reset) level 104b.

Figure 5:
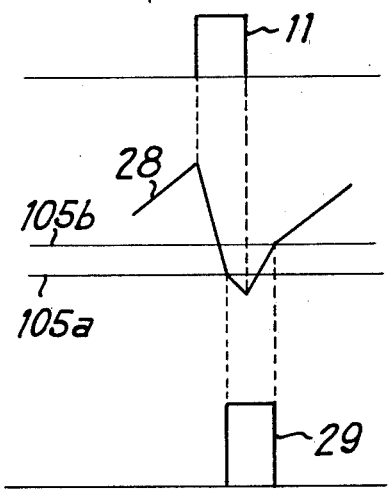
FIG. 5 is a graph showing the error detection and device control signals in the case in which the true rate of flow is inadequate.

As is apparent from FIG. 5, the comparator 105 operates in symmetrical manner, its activation level 105a being lower than its deactivation level 105b, but in the closing direction. Nevertheless, the closing pulses 29 it feeds to the motor 12 are relatively great in such manner as to allow of a very fast closing of the clamping system, which is required if for example an obstruction in the tubing were suddenly to be removed. Moreover, the level 28 may downwardly exceed the activation level 105a, contrary to the mode of operation of the comparator 104.

The charging and discharging actions of the capacitor are performed at constant current, and therefore the minimum and maximum levels of the voltage of the capacitor constitute a precise measure of the difference between the true rate of flow measured and a reference rate of flow. Moreover, use is made only of the maximum level of the said voltage for valve opening, the minimum level being set aside for valve closing. This simplifies the circuits and improves their effectiveness.

The assembly includes other features to improve its practical operation.

Firstly, a connection 30, 31 is provided between the output of each comparator 104, 105 and the junction between the resistors 20 and 21 to secure the stabilisation of the discharge current of the capacitor 18 upon changing to the "high" condition of the comparators — in such manner as to establish the amplitude of the pulses 27, 29 correctly and to render this amplitude independent, with respect to adjustment, from the potentiometer 17.

Secondly, a system is provided for blocking the pulses 27, 29 by means of contacts 32, 33 which detect the opening and closing limits of the motor 12. The control pulses 27, 28 of the comparators 104, 105 are amplified by the transistors 34 before being applied to the motor 12.

Thirdly, a screened detecting diode 35 and a transmitting diode 36 serve to detect the presence of air in the feed tube 3 (see FIG. 1). The signal collected by this electrode 35 is detected and amplified by the circuit 106 and is arranged to trigger a very low frequency oscillator 107 forming a sonic alarm with a relay armature 107.

The circuits are switched on by the closing of a switch 37 which is associated with a time-delay circuit 108 followed by a bistable flipflop 109. When the apparatus is switched on, these units allow the motor 12 to accelerate to maximum speed, in the direction which opens the throttle valve, until the first dropfalls into the chamber 2.

The drops no longer fall if, for any reason, the liquid no longer passes correctly through the tubing. The motor 12 then opens the valve. When the maximum degree of opening is reached, the end-of-travel contact arm 32a bears on the end-of-opening-travel contact 32 and the warning oscillator 107 is activated because of the earthing of the point 38 of the oscillator.

The desirable or nominal rate of flow is displayed by means of the linear-function potentiometer 17. This potentiometer 17 is supplied with a constant voltage. Its tapping receives a fraction of this voltage, this fraction depending only on the position of the tapping and not on th ohmic rating of the potentiometer. This voltage is applied to the error signal generator circuit 103. A stationary pointer 42 (FIG. 1) is positoned in alignment on an logarithmic scale 39b which is graduated in drops/minute and whose deflection is selected according to requirements.

To simplify the operation of the device, it is convenient to associate with this scale a graduated slider system rendering it possible to display the actual volume it is desired to pass through, and the time which should elapse. A third datum should however be fed into the device: this is the volume of each drop.

Therefore, the first graduated slider 39 is integral with the tapping of the potentiometer 17 and, as explained, its position controls drops/minute. An logarithmic time scale 39a and the rate of flow scale 39b in drops/minute are scribed on the graduated slider 39.

A second graduated slider 40 comprises two scales, an logarithmic progression scale 40a for the volume, and a scale 40b, also of the logarithmic progression type, for the volume of the drops. The graduated slider 40 may be displaced in such manner as to establish coincidence between the volume of the drops and a reference pointer 41 secured to the case 1. These two graduated sliders 39 and 40 are arranged in such manner that the volume scale 40a and the time scale 39a are side-by-side.

The system is devised in such manner that it is sufficient to position the selected volume read off from scale 40a and the selected period read off from scale 39a in registering relation to each other by displacing the slider 39, whereupon the number of drops per minute is calculated and displayed immediately. The user thus no longer has to make scientific calculations and the application of the device is therefore simplified.

Figure 6:
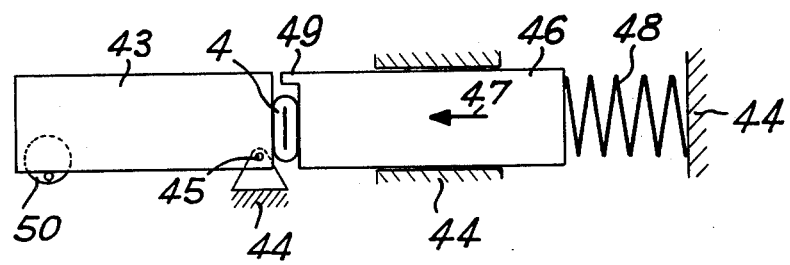
FIG. 6 is a plan view of a throttle valve system of the device.
Figure 7:
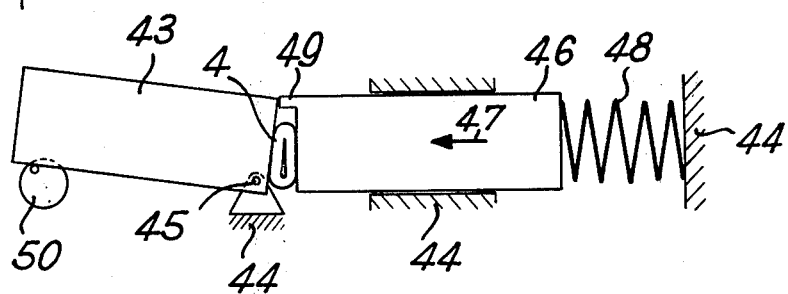
FIG. 7 illustrates the same view as FIG. 6, the valve being in the open position.

FIGS. 6 and 7 show a throttle valve comprising two clamping elements or jaws 43 and 46 which are positioned at either side of the flexible delivery tube 4 of the transfusion tubing.

The clamping element 43 is pivotally arranged on a frame 44 around an axis 45 which is not at right angles to the plane of contact of the element 43 with the flexible tube 4 and is arranged to be turned around this axis 45 by the driving motor in response to the error signal.

The second clamping element 46 is slidably installed on the frame along an axis 47 which is not parallel to the plane of contact of the element 46 with the flexible tube 4 and a resilient member 48 impels the second element 46 towards the first element 43.

The pivot spindle 45 of the first clamping element 43 is substantially parallel to the axis of the flexible tube 4 whereas the sliding axis 47 of the second clamping element 46 is substantially at right angles to the axis of the flexible tube 4.

A projection 49 at one extremity of the surface of the clamping element 46 adjacent to the flexible tube 4 is positioned to be able to come into direct contact with the other clamping element 43.

The first clamping element 43 is turned about axis 45 by means of an eccentric 50 driven by the driving motor.

The pivot spindle 45 of the first clamping element 43 is situated at the extremity of the element, adjacent to the flexible tube 4 and at the level of one extremity of the surface of the element in contact with the flexible tube 4.

Each clamping element has the form of an elongated plate one of whose edge surfaces is in contact with the flexible tube, the two plates being positioned to be substantially co-planar with a plane at right angles to the flexible tube 4.

The clamping system thus operates according to the principle of tilting one jaw 43, 46 with respect to the other jaw, the jaws being thrust against each other by a constant force.

At the start, the jaws 43, 46 have their axes parallel to each other (FIG. 6). A constant force (for example 2.5 kgs) is applied on one of them by means of the spring 48 bearing on the frame 44. The tube 4 is squashed and prevents passage of liquid.

When the other jaw 43 turns on the spindle, it tilts with respect to the other jaw, resulting in a very gradual opening of the tube 4 (FIG. 7). This opening is a function of the angle of tilt of the jaw 43 with respect to the jaw 46, but it is independent of the thickness of the tube. This makes it possible to limit the displacement of the motor to the range which is strictly necessary. The servo system may thus easily be stabilised.

The eccentric 50 may be driven by the motor via a reduction gear. The return force exerted on the tiltable jaw 43 by the force applied by the spring 48 on the other jaw 46 is transmitted to the eccentric 50. This exerts a permanent moment on the output train of the reduction gear and this permanent moment renders it possible to eliminate backlash in the gears and enables the device to operate correctly. A slight backlash at this point would manifest itself in an unstable operation of the servo-system.

Nevertheless, to prevent excessive creepage of the plastics material tube 4 at its most highly compressed point, one of the jaws 46 has a stop or projection 49 which limits the mutual approach of the two jaws.

This clamping system also has the advantage of establishing the height of the tube with respect to the clamping system, notwithstanding the degree of opening: the clamping of the tube 4 prevents any slipping of the device 1 along the perfusion tubing.

Various modifications will be apparent to those skilled in the art without departing from the scope of the invention.

What is claimed is:

1. In a liquid flow control apparatus the combination comprising: means defining a liquid flow path along part of which flow takes place in the form of liquid falling drops each of a determined volume; flow control valve means in the said path; a drop detector sensing the passage of each drop in the said part and producing a first signal which is representative of the actual number of drops per unit of time; setting means for producing a second signal which is representative of a desired number of drops per unit of time, said setting means including one movable member and means for converting a displacement of said member into a signal representative of this displacement; and servo control means for comparing said first and second signals to produce an error signal for adjusting the valve means in a sense such as to tend to control the number of drops per unit of time at the desired value, and computation and displaying means including:
   (a) linear to exponential signal converting means converting said signal representative of the displacement of said one movable member into the exponential thereof, this converted signal constituting said second signal, and
   (b) a second movable member movable, independently of the said one movable member,
   (c) means for setting said second movable member in a position representative of the value of the logarithm of the size of each of said drops, said one movable member carrying a first logarithmic scale graduated with respect to the time duration during which the liquid has to be injected and said second movable member carrying a second logarthmic scale graduated with respect to the volume of liquid to be injected, these movable members being arranged so as these scales are juxtaposed each other, whereby the desired number of drops per unit of time can be set by putting the value of the volume of liquid to be injected read off from said second logarithmic scale in registering relation with the value of the time during which this volume of liquid has to be injected, read off from said first logarithmic scale.

2. The combination according to claim 1, in which the drop detector produces electrical pulses at a frequency which is a function of the actual number of drops per unit of time, and the servo control means includes capacitive means connected to the rate of flow detector and to the setting means so that its charge is altered in one sense by an electrical signal dependent on the desired rate of flow signal and is altered in the opposite sense by the said pulses, and means responsive to the mean charge on the capacitive means for producing the said error signal.

3. The combination according to claim 2, including
   a two-input operational amplified,
   means connecting the capacitive means between the output and one input of the operational amplifier which is arranged to operate in unsaturated mode,
   means connecting the said one input of the amplifier to receive the said measurement pulses,
   a first signal regulating device connecting the said one input of the amplifier to a datum potential, and
   a second signal regulating device which is controlled in dependence on the second signal and connecting the other input of the operational amplifier to the said datum potential.

4. The combination according to claim 3, in which the said second signal regulating device is in the form of a linear to exponential three-terminal signal converting device to which the second signal, in the form of a linearly variable voltage, is applied.

5. The combination according to claim 2, in which the flow control valve means comprises
   a throttle valve,
   a reversible motor arranged to control the throttle valve, and two flip-flop circuits responsive to the mean level of charge on the said capacitive means whereby respectively to supply signals for energising the motor in opposite directions so as to open or close the throttle valve.

6. The combination according to claim 1, in which the flow control valve means comprises a throttle valve in the path of the liquid flow for adjustably throttling the flow, the throttle valve comprising
   a flexible tube for carrying the flow,
   two relatively movable clamping elements in contact with opposite sides of the flexible tube and relatively movable towards and away from each other so as to provide a variable throttling effect on the said tube,
   one of the clamping elements being pivoted about an axis which is not at right angles to the plane of contact of the said element with the flexible tube and being pivotable about this axis in dependence on the said error signal, and
   the second clamping element being slidable along an axis which is not parallel to its plane of contact with the flexible tube and being resiliently biased towards the tube.

* * * * *